(12) United States Patent
Yamazaki et al.

(10) Patent No.: US 7,714,141 B2
(45) Date of Patent: May 11, 2010

(54) PROCESSES FOR PRODUCTION OF OPTICALLY ACTIVE PPAR-ACTIVATING COMPOUNDS AND INTERMEDIATES FOR PRODUCTION THEREOF

(75) Inventors: Yukiyoshi Yamazaki, Higashimurayama (JP); Takaaki Araki, Higashimurayama (JP); Minoru Koura, Kawagoe (JP); Kimiyuki Shibuya, Tokorozawa (JP)

(73) Assignee: Kowa Co., Ltd., Nagoya-shi (JP)

( * ) Notice: Subject to any disclaimer, the term of this patent is extended or adjusted under 35 U.S.C. 154(b) by 257 days.

(21) Appl. No.: 11/912,811

(22) PCT Filed: May 30, 2006

(86) PCT No.: PCT/JP2006/310755

§ 371 (c)(1),
(2), (4) Date: Oct. 26, 2007

(87) PCT Pub. No.: WO2006/129649

PCT Pub. Date: Dec. 7, 2006

(65) Prior Publication Data

US 2009/0076280 A1    Mar. 19, 2009

(30) Foreign Application Priority Data

May 31, 2005  (JP)  ............... 2005-159261
Jun. 16, 2005  (JP)  ............... 2005-176663

(51) Int. Cl.
*C07D 263/58*  (2006.01)
*C07D 277/82*  (2006.01)
*C07D 235/30*  (2006.01)

(52) U.S. Cl. ............ 548/222; 548/161; 548/307.4

(58) Field of Classification Search ............... 548/161, 548/222, 307.4
See application file for complete search history.

(56) References Cited

U.S. PATENT DOCUMENTS

| | | | |
|---|---|---|---|
| 6,653,334 B1 | 11/2003 | Yamazaki et al. | ........... 548/222 |
| 7,109,226 B2 * | 9/2006 | Yamazaki et al. | ........... 514/375 |
| 7,183,295 B2 * | 2/2007 | Yamazaki et al. | ........... 514/339 |

FOREIGN PATENT DOCUMENTS

| | | |
|---|---|---|
| JP | 2005 510450 | 4/2005 |
| JP | 2005 515882 | 6/2005 |
| WO | 2005 023777 | 3/2005 |

OTHER PUBLICATIONS

U.S. Appl. No. 11/816,921, filed Aug. 23, 2007, Yamazaki et al.

(Continued)

*Primary Examiner*—Rebecca L Anderson
*Assistant Examiner*—Matthew P Coughlin
(74) *Attorney, Agent, or Firm*—Oblon, Spivak, McClelland, Maier & Neustadt, L.L.P.

(57) ABSTRACT

The invention provides a process for producing an optically active butyric acid compound and a production intermediate therefore at high yield and high purity.

The present invention provides a process for producing Compound (6), including reacting Compound (1) with optically active 2-trifluoromethanesulfonyloxybutyrolactone (2a) in the presence of a base or reacting optically active 2-hydroxy-butyrolactone (2b) under Mitsunobu reaction conditions, to thereby form Compound (3); reacting Compound (3) with an alcohol and a halogenating agent, to thereby form Compound (4); dehalogenating Compound (4), to thereby form Compound (5); and de-esterifying Compound (5).

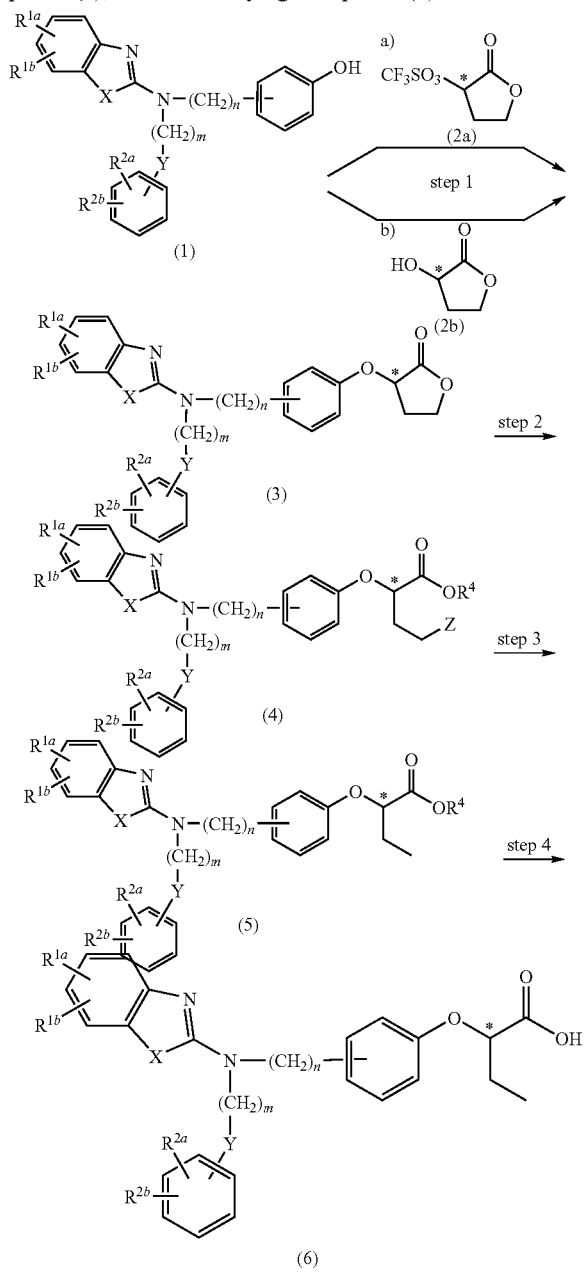

6 Claims, No Drawings

OTHER PUBLICATIONS

U.S. Appl. No. 11/816,472, filed Aug. 16, 2007, Yamazaki et al.

Isabelle Issemann, et al., "Activation of a member of the steroid hormone receptor superfamily by peroxisome proliferators", Nature, vol. 347, Oct. 18, 1990, pp. 645-650.

Christine Dreyer, et al., "Control of the Peroxisomal β-Oxidation Pathway by a Novel Family of Nuclear Hormone Receptors", Cell, vol. 68, Mar. 6, 1992, pp. 879-887.

"A Unified Nomenclature System for the Nuclear Receptor Superfamily", Cell, vol. 97, Apr. 16, 1999, pp. 161-163.

Kristina Schoonjans, et al., "The peroxisome proliferator activated receptors (PPARs) and their effects on lipid metabolism and adipocyte differentiation", Biochimica et Biophysica Acta, vol. 1302, 1996, pp. 93-109.

Timothy M. Willson, et al., "The PPARs: From Orphan Receptors to Drug Discovery", Journal of Medicinal Chemistry, vol. 43, No. 4, Feb. 24, 2000, pp. 527-550.

Frank J. Gonzalez, et al., Mechanism of Action of the Nongenotoxic Peroxisome Proliferators: Role of the Peroxisome Proliferator-Activated Receptor α, Journal of the National Cancer Institute, vol. 90, No. 22, Nov. 18, 1998, pp. 1702-1709.

Jean-Charles Fruchart, et al., "Peroxisome proliferator-activated receptor-alpha activators regulate genes governing lipoprotein metabolism, vascular inflammation and atherosclerosis", Current Opinion in Lipidology, vol. 10, 1999, pp. 245-257.

Johan Auwerx, et al., "Regulation of Triglyceride Metabolism by PPARs: Fibrates and Thiazolidinediones have Distinct Effects", Journal of Atherosclerosis and Thrombosis, vol. 3, No. 2, Oct. 17, 1996, pp. 81-89.

Bart Staels, et al., "Role of PPAR in the Pharmacological Regulation of Lipoprotein Metabolism by Fibrates and Thiazolidinediones", Current Pharmaceutical Design, vol. 3, No. 1, 1997, pp. 1-14.

Inés Pineda, et al., "Peroxisome proliferator-activated receptor alpha in metabolic disease, inflammation, atherosclerosis and aging", Current Opinion in Lipidology, vol. 10, 1999, pp. 151-159.

Joseph Vamecq, et al., "Medical significance of peroxisome proliferator-activated receptors", The Lancet, vol. 354, Jul. 10, 1999, pp. 141-148.

Sander J. Robins, "PPAR$\delta$ ligands and clinical trials: cardiovascular risk reduction with fibrates", Journal of Cardiovascular Risk, vol. 8, No. 4, 2001, pp. 195-201.

The Lancet, vol. 349, Mar. 29, 1997, p. 952.

Jennifer L. Oberfield, et al., "A peroxisome proliferator-activated receptor γ ligand inhibits adipocyte differentiation", Proc. Natl. Acad. Sci., vol. 96, May 1999, pp. 6102-6106.

Harold M. Wright, et al., "A Synthetic Antagonist for the Peroxisome Proliferator-activated Receptor γ Inhibits Adipocyte Differentiation", The Journal of Biological Chemistry, vol. 275, No. 3, Jan. 21, 2000, pp. 1873-1877.

Toshimasa Yamauchi, et al., "Inhibition of RXR and PPAR γ ameliorates diet-induced obesity and type 2 diabetes", The Journal of Clinical Investigation, vol. 108, No. 7, Oct. 2001, pp. 1001-1013.

Yaacov Barak, et al., Effects of peroxisome proliferator-activated receptor δ on placentation, adiposity, and colorectal cancer, Proc. Natl. Acad. Sci., vol. 99, No. 1, Jan. 8, 2002, pp. 303-308.

* cited by examiner

PROCESSES FOR PRODUCTION OF OPTICALLY ACTIVE PPAR-ACTIVATING COMPOUNDS AND INTERMEDIATES FOR PRODUCTION THEREOF

CROSS REFERENCE TO RELATED APPLICATIONS

This application is the National Stage of International Application No. PCT/JP2006/310755, filed May 30, 2006, which claims the benefit under 35 U.S.C. 119(a)-(d) of Japanese Application No's. 2005-176663 and 2005-159261, filed Jun. 16, 2005 and May 31, 2005, respectively.

TECHNICAL FIELD

The present invention relates to a method for producing a compound which activates PPARs (peroxisome proliferator-activated receptors) and which is a useful drug for preventing and/or treating diseases including hyperlipidemia, arteriosclerosis, and diabetes; and to a method for producing production intermediate for the production thereof.

BACKGROUND ART

PPARs are known to be a family of nuclear receptors, and three sub-types thereof (α, γ, δ) have already been identified (Non-Patent Documents 1 to 5). Among the three sub-types, PPARα is expressed primarily in the liver and is known to be activated by a plasticizer or a fibrate-type drug such as Wy 14643 or a commercially available pharmaceutical; e.g., clofibrate, fenofibrate, bezafibrate, or gemfibrozil (Non-Patent Documents 6 and 7).

In mammals, activation of PPARα is known to promote β oxidation of fatty acids and to lower blood triglyceride level, and in humans, blood lipid levels such as low-density lipoprotein (LDL) cholesterol level and very low-density lipoprotein (VLDL) cholesterol level are known to decrease. Thus, a PPARα-activating agent is considered a useful drug for preventing and/or treating diseases such as hyperlipidemia. In addition, the PPARα-activating agent, which increases high-density lipoprotein (HDL) cholesterol level and, in blood vessels, suppresses expression of VCAM-1 (a type of cell adhesion factor), is considered to be useful for preventing and/or treating diseases such as arteriosclerosis, and for preventing and/or treating diseases such as diabetes, inflammatory diseases, and heart diseases (Non-Patent Documents 5 and 7 to 14).

Activation of PPARγ in humans has been reported to cause adverse effects of increasing the amount of fat and body weight and causing obesity (Non-Patent Document 13). Recent studies have also reported that a PPARγ antagonist possibly improves insulin resistance (Non-Patent Documents 14 to 16). A document reports that activation of PPARδ causes lipid accumulation (Non-Patent Document 17). Therefore, a PPARα-selective activator exhibiting low PPARγ and PPARδ activities are considered to be a promising agent for prevention and/or treatment, without entailing obesity or increase in body weight, of pathological conditions including hyperlipidemia, arteriosclerosis, diabetes, complications of diabetes, inflammation, and heart diseases.

Under such circumstances, the present inventors previously found that compounds represented by formula (A):

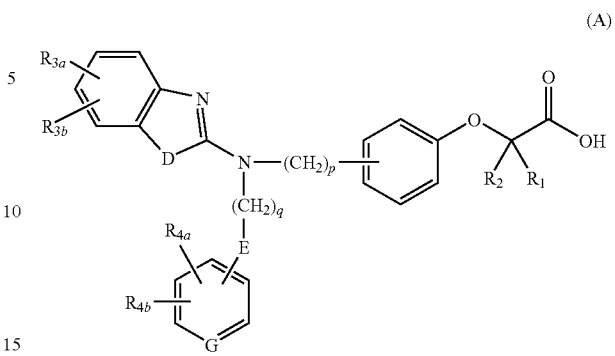

(wherein $R_1$ and $R_2$, which may be identical to or different from each other, each represent a hydrogen atom, a methyl group, or an ethyl group; $R_{3a}$, $R_{3b}$, $R_{4a}$, and $R_{4b}$, which may be identical to or different from one another, each represent a hydrogen atom, a halogen atom, a nitro group, a hydroxyl group, a $C_{1-4}$ alkyl group, a trifluoromethyl group, a $C_{1-4}$ alkoxy group, a di-$C_{1-4}$ alkylamino group, a $C_{1-4}$ alkylsulfonyloxy group, a $C_{1-4}$ alkylsulfonyl group, a $C_{1-4}$ alkylsulfinyl group, or a $C_{1-4}$ alkylthio group, wherein $R_{3a}$ and $R_{3b}$ may be linked to each other to form an alkylenedioxy group, or $R_{4a}$ and $R_{4b}$ may be linked to each other to form an alkylenedioxy group; D represents an oxygen atom, a sulfur atom, or N—$R_5$ (wherein $R_5$ represents a hydrogen atom, a $C_{1-4}$ alkyl group, a $C_{1-4}$ alkylsulfonyl group, or a $C_{1-4}$ alkyloxycarbonyl group); E represents an oxygen atom, an $S(O)_t$ group (wherein t is an integer of 0 to 2), a carbonyl group, a carbonylamino group, an aminocarbonyl group, a sulfonylamino group, or an aminosulfonyl group; G represents CH or N; p is an integer of 1 to 6; and q is an integer of 2 to 6) and salts thereof selectively activate PPARα, and therefore are useful for the prevention and/or treatment, without entailing obesity or increase in body weight, of pathological conditions including hyperlipidemia, arteriosclerosis, diabetes, complications of diabetes, inflammation, and heart diseases, and filed a patent application (Patent Document 1).

The phenyl ether moiety of the compound represented by formula (A) may be produced through phenyl-etherification of a corresponding phenol form as shown below. Patent Document 1 discloses the following applicable procedures: 1) phenyl-etherification in which a phenol form is reacted with a 2-halocarboxylic acid ester in the presence of a base (reaction steps A-1, B-2, C-3, D-1, and E-3); 2) phenyl-etherification in which the OH group of a 2-hydroxycarboxylic acid ester is transformed (e.g., mesylate or tosylate) to a leaving group such as a methanesulfonyloxy group or a p-toluenesulfonyloxy group, and the product is reacted with a phenol form in the presence of a base (reaction steps F-4 and J-4); and 3) Mitsunobu reaction employing a phenol form and a 2-hydroxycarboxylic acid ester.

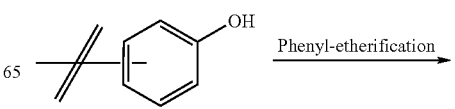

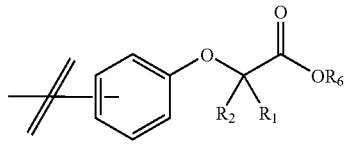

In the above formula, $R_1$ and $R_2$ have the same meanings as defined above; and $R_6$ represents a group such as $C_{1-4}$ alkyl.

Patent Document 1: WO 05/23777 pamphlet
Non-Patent Document 1: Nature, 347, 645-650, 1990
Non-Patent Document 2: Cell, 68, pp. 879-887, 1992
Non-Patent Document 3: Cell, 97, pp. 161-163, 1999
Non-Patent Document 4: Biochim. Biophys. Acta., 1302, pp. 93-109, 1996
Non-Patent Document 5: Journal of Medicinal Chemistry, 43, pp. 527-550, 2000
Non-Patent Document 6: Journal of the National Cancer Institute, 90, 1702-1709, 1998
Non-Patent Document 7: Current Opinion in Lipidology, 10, pp. 245-257, 1999
Non-Patent Document 8: Journal of Atherosclerosis and Thrombosis, 3, pp. 81-89, 1996
Non-Patent Document 9: Current Pharmaceutical Design, 3, pp. 1-14, 1997
Non-Patent Document 10: Current Opinion in Lipidology, 10, pp. 151-159, 1999
Non-Patent Document 11: The Lancet, 354, pp. 141-148, 1999
Non-Patent Document 12: Journal of Cardiovascular Risk, 8, pp. 195-201, 2001
Non-Patent Document 13: The Lancet, 349, pp. 952, 1997
Non-Patent Document 14: Proc. Natl. Acad. Sci., 96, pp. 6102-6106, 1999
Non-Patent Document 15: The Journal of Biological Chemistry, 275, pp. 1873-1877, 2000
Non-Patent Document 16: J. Clin. Invest., 108, 1001-1013,
Non-Patent Document 17: Proc. Natl. Acad. Sci., 99, pp. 303-308, 2002

DISCLOSURE OF THE INVENTION

Problems to be Solved by the Invention

An object of the present invention is to provide an optically active butyric acid compound included in the aforementioned formula (A). Another object is to provide a process for producing a production intermediate therefore at high yield and high purity.

Means for Solving the Problems

The present inventors have carried out extensive studies on a useful production process for an optically active butyric acid compound represented by formula (6), and have found that the compound of formula (6) (hereinafter may be referred to as Compound (6), and the like rule applies throughout the specification) can be produced without impairing optical purity through the following reaction scheme:

Specifically, optically active 2-trifluoromethanesulfonyloxybutyrolactone (2a) is phenyl-etherified with Compound (1) in the presence of a base, or optically active 2-hydroxybutyrolactone (2b) is phenyl-etherified with Compound (1) under Mitsunobu reaction conditions, to thereby yield Compound (3) at high yield and high purity (step 1). The lactone ring of Compound (3) is opened to form Compound (4) (step 2). Compound (4) is dehalogenated to form Compound (5) (step 3), followed by de-esterification (step 4).

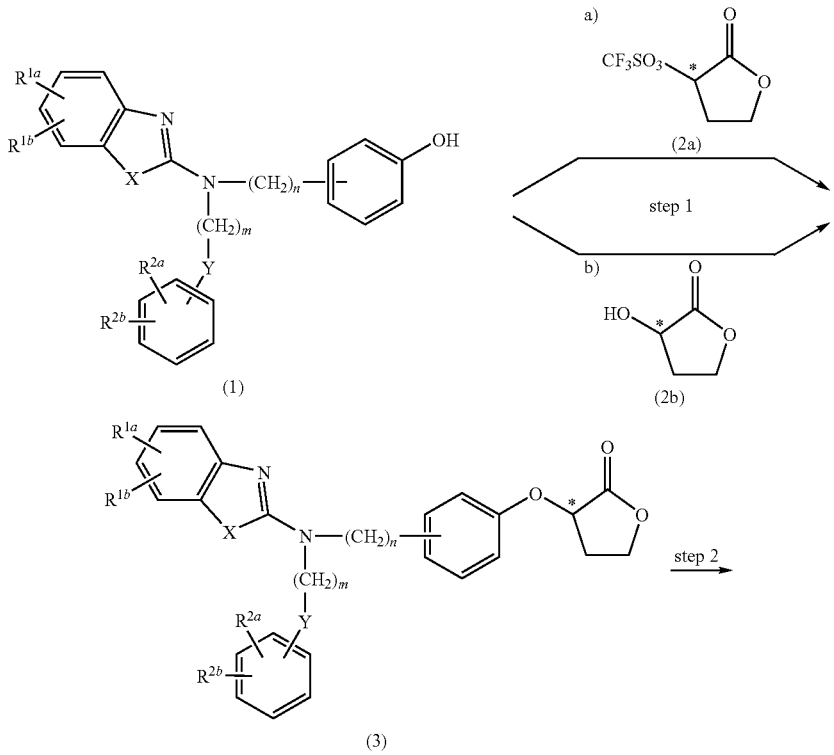

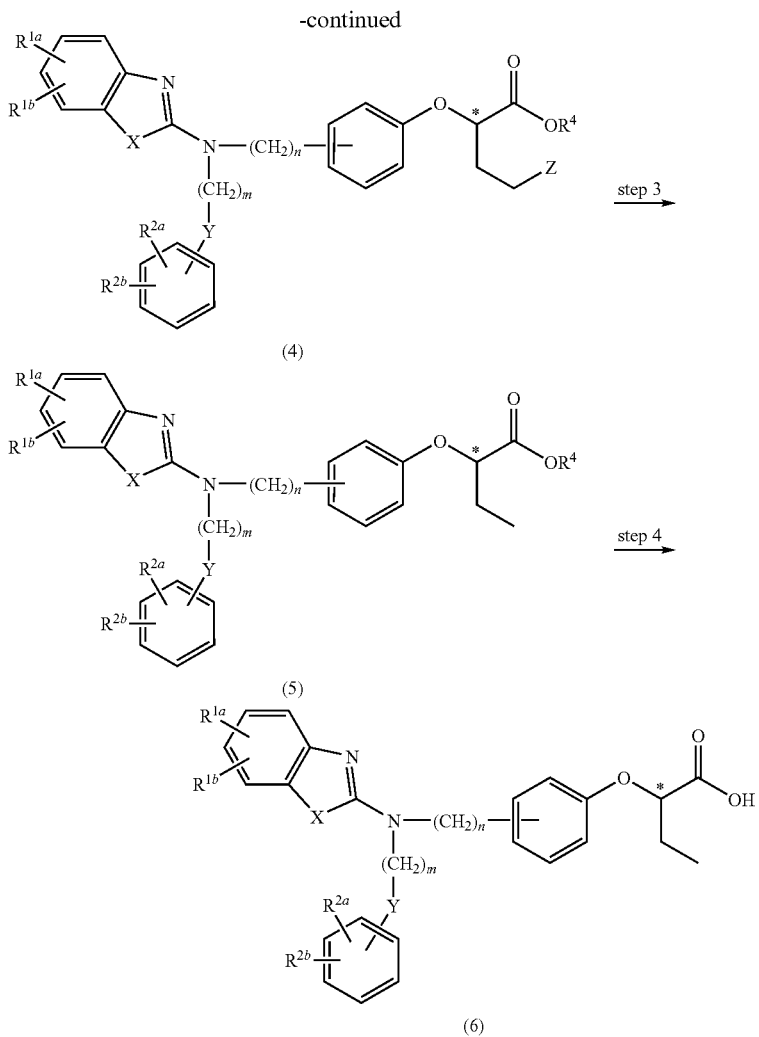

(wherein $R^{1a}$, $R^{2b}$, $R^{2a}$, and $R^{2b}$, which may be identical to or different from one another, each represent a hydrogen atom, a halogen atom, a nitro group, a $C_{1-4}$ alkyl group, a trifluoromethyl group, a $C_{1-4}$ alkoxy group, a di-$C_{1-4}$ alkylamino group, a $C_{1-4}$ alkylsulfonyloxy group, a $C_{1-4}$ alkylsulfonyl group, or a $C_{1-4}$ alkylthio group, wherein $R^{1a}$ and $R^{1b}$ may be linked to each other to form an alkylenedioxy group, or $R^{2a}$ and $R^{2b}$ may be linked to each other to form an alkylenedioxy group; $R^4$ represents a $C_{1-4}$ alkyl group or a $C_{6-10}$ aryl-$C_{1-3}$ alkyl group; X represents an oxygen atom, a sulfur atom, or N—$R^3$ (wherein $R^3$ represents a hydrogen atom or a $C_{1-4}$ alkyl group); Y represents an oxygen atom, an S(O)$_l$ group (wherein l is an integer of 0 or 2), a carbonyl group, or a carbonylamino group; Z represents a halogen atom; n is an integer of 1 to 6; m is an integer of 2 to 6; and the symbol "*" denotes asymmetric S or R configuration.

Accordingly, the present invention is directed to a process for producing Compound (3), characterized in that the process comprises reacting Compound (1) with optically active 2-trifluoromethanesulfonyloxybutyrolactone (2a) in the presence of a base or reacting optically active 2-hydroxybutyrolactone (2b) under Mitsunobu reaction conditions.

The present invention is also directed to a process for producing Compound (4), characterized in that the process comprises reacting Compound (1) with optically active 2-trifluoromethanesulfonyloxybutyrolactone (2a) in the presence of a base or reacting optically active 2-hydroxybutyrolactone (2b) under Mitsunobu reaction conditions, to thereby form Compound (3); and reacting Compound (3) with an alcohol represented by $R^4$—OH (wherein $R^4$ has the same meaning as defined above) and a halogenating agent.

The present invention is also directed to a process for producing Compound (5), characterized in that the process comprises reacting Compound (1) with optically active 2-trifluoromethanesulfonyloxybutyrolactone (2a) in the presence of a base or reacting optically active 2-hydroxybutyrolactone (2b) under Mitsunobu reaction conditions, to thereby form Compound (3); reacting Compound (3) with an alcohol represented by $R^4$—OH (wherein $R^4$ has the same meaning as defined above) and a halogenating agent, to thereby form Compound (4); and dehalogenating Compound (4).

The present invention is also directed to a process for producing Compound (6), characterized in that the process comprises reacting Compound (1) with optically active 2-trifluoromethanesulfonyloxybutyrolactone (2a) in the presence of a base or reacting optically active 2-hydroxybutyrolactone (2b) under Mitsunobu reaction conditions, to thereby form Compound (3); reacting Compound (3) with an alcohol represented by R⁴—OH (wherein R⁴ has the same meaning as defined above) and a halogenating agent, to thereby form Compound (4); and dehalogenating Compound (4), to thereby form Compound (5); and de-esterifying Compound (5).

The present invention is also directed to Compound (3).
The present invention is also directed to Compound (4).

EFFECTS OF THE INVENTION

The process of the present invention realizes high-yield and high-optical-purity production of an optically active butyric acid compound (6), which is a PPARα-selective activator and which can prevent and/or treat, without entailing obesity or increase in body weight, pathological conditions including hyperlipidemia, arteriosclerosis, diabetes, complications of diabetes, inflammation, and heart diseases, and also an production intermediate therefore.

BEST MODES FOR CARRYING OUT THE INVENTION

Examples of preferred substituents in the present invention represented by $R^{1a}$, $R^{1b}$, $R^{2a}$, and $R^{2b}$ in formulas (1), (3), (4), (5), and (6) will next be described.

Examples of the halogen atom include a fluorine atom and a chlorine atom.

Examples of the $C_{1-4}$ alkyl group include methyl, ethyl, n-propyl, isopropyl, and n-butyl, with methyl being particularly preferred.

Examples of the $C_{1-4}$ alkoxy group include methoxy, ethoxy, n-propoxy, isopropoxy, and n-butoxy, with methoxy being particularly preferred.

Examples of the di-$C_{1-4}$ alkylamino group include dimethylamino, diethylamino, and diisopropylamino, with dimethylamino being particularly preferred.

Examples of the $C_{1-4}$ alkylsulfonyloxy group include methylsulfonyloxy and ethylsulfonyloxy, with methylsulfonyloxy being particularly preferred.

Examples of the $C_{1-4}$ alkylsulfonyl include methylsulfonyl and ethylsulfonyl, with methylsulfonyl being particularly preferred.

Examples of the $C_{1-4}$ alkylthio group include methylthio and ethylthio, with methylthio being particularly preferred.

Examples of the alkylenedioxy group, which is formed through linkage of $R^{1a}$ and $R^{1b}$ or linkage of $R^{2a}$ and $R^{2b}$, include methylenedioxy and ethylenedioxy, with methylenedioxy being particularly preferred.

Examples of the $C_{1-4}$ alkyl group represented by R⁴ in formulas (4) and (5) in the present invention include methyl, ethyl, n-propyl, isopropyl, n-butyl, isobutyl, and t-butyl, with methyl and ethyl being particularly preferred. Examples of the $C_{6-10}$ aryl-$C_{1-3}$ alkyl group represented by R⁴ in formulas (4) and (5) in the present invention include benzyl, phenethyl, phenylpropyl, and naphthylethyl, with phenethyl being particularly preferred.

Examples of the halogen atom represented by Z in formula (4) in the present invention include a chlorine atom, a bromine atom, and an iodine atom. Of these, a bromine atom and an iodine atom are particularly preferred, with an iodine atom being particularly preferred.

In formulas (1), (3), (4), (5), and (6) in the present invention, X represents an oxygen atom, a sulfur atom, or N—R³ (wherein R³ is a hydrogen atom or a $C_{1-4}$ alkyl group), with an oxygen atom being preferred. Y represents an oxygen atom, an S(O)ₗ group (wherein l is an integer of 0 or 2, preferably 2), a carbonyl group, or a carbonylamino group, with an oxygen atom being preferred.

In formulas (1), (3), (4), (5), and (6) in the present invention, n is an integer of 1 to 6, preferably 1 to 3, and m is an integer of 2 to 6, preferably 2 to 4, particularly preferably 2 or 3.

Among the compounds represented by formulas (1), (3), (4), (5), and (6) in the present invention, particularly preferred are compounds in which $R^{1a}$ and $R^{1b}$ each are a hydrogen atom; one of $R^{2a}$ and $R^{2b}$ is a hydrogen atom and the other is a methoxy group; X and Y each are an oxygen atom; m is 3; and n is 1. Among the compounds represented by formulas (4) and (5), preferred are compounds in which R⁴ is methyl, ethyl, or phenethyl. Among the compound represented by formula (4), more preferred are compounds in which Z is a bromine atom or an iodine atom.

Hereinafter, reaction steps included in the process of the present invention will be described.

1. Step 1-a

In step 1-a, a phenol form (Compound (1)) is reacted with optically active 2-trifluoromethanesulfonyloxybutyrolactone (2a) in the presence of a base for phenyl-etherification, to thereby form a lactone form (Compound (3)).

The reaction is performed in an appropriate solvent. Examples of preferred solvents include dichloromethane, chloroform, 1,2-dichloroethane, acetonitrile, and propionitrile. Of these, dichloromethane, chloroform, acetonitrile, and propionitrile are more preferred, with dichloromethane and chloroform being particularly preferred.

Examples of the base include an organic base such as pyridine, triethylamine, or diisopropylethylamine; and an inorganic base such as sodium carbonate, potassium carbonate, or cesium carbonate. Of these, triethylamine, diisopropylethylamine, sodium carbonate, and potassium carbonate are preferred, with triethylamine being particularly preferred.

The reaction may be performed at 0° C. to 50° C. The reaction temperature is preferably 10° C. to 40° C., particularly preferably 20° C. to 30° C. The reaction time is 1 to 24 hours, preferably 2 to 6 hours.

If required, the reaction may be performed in an inert gas atmosphere such as argon or nitrogen.

Optically active 2-trifluoromethanesulfonyloxybutyrolactone (2a) employed in this step is a novel compound which has never been disclosed in the literature. The compound may be produced through reaction between optically active 2-hydroxybutyrolactone and trifluoromethanesulfonyl chloride or trifluoromethanesulfonic acid anhydride in the presence of a base in a solvent (see Production Example 1).

Examples of the solvent employed in this step include dichloromethane, chloroform, and 1,2-dichloroethane, with dichloromethane and chloroform being preferred. Examples of the base include organic bases such as pyridine, picoline, lutidine, collidine, triethylamine, and diisopropylethylamine. Among them, pyridine, lutidine, and triethylamine are preferred, with pyridine and lutidine being particularly preferred. The reaction may be performed at -78° C. to 25° C. The reaction temperature is preferably -30° C. to 10° C., particularly preferably -10° C. to 0° C. The reaction time is 0.5 to 4 hours, preferably 0.5 to 1.5 hours.

2. Step 1-b

In step 1-b, a phenol form (Compound (1)) is reacted with optically active 2-hydroxybutyrolactone (2b) under Mitsunobu reaction, to thereby form a lactone form (Compound (3)).

Mitsunobu reaction is a dehydration-condensation reaction between an alcohol and a nucleophilic reagent in the presence of an azo reagent and a phosphorus-containing reagent. Mitsunobu reaction is performed in an appropriate solvent. Examples of preferred solvents include toluene, tetrahydrofuran, dioxane, tert-butyl methyl ether, acetonitrile, propionitrile, N,N-dimethylformamide, and N,N-dimethyl-2-imidazolidinone. Of these, toluene and tetrahydrofuran are more preferred, with toluene being particularly preferred.

Examples of the phosphorus-containing reagent include triphenylphosphine, tri(o-tolyl)phosphine, tri(p-fluorophenyl)phosphine, tris(2,4,6-trimethoxyphenyl)phosphine, trimethylphosphine, and tri(n-butyl)phosphine, with triphenylphosphine being particularly preferred.

Examples of the azo reagent include diethyl azodicarboxylate (DEAD), diisopropyl azodicarboxylate (DIAD), di-tert-butyl azodicarboxylate (DBAD), tetramethylazodicarboxamide (TMAD), tetraisopropylazodicarboxamide (TIPA), azodicarbonyldipiperidine (ADDP), and dimethylhexahydrotetrazocinedione (DHTD). Of these, diethyl azodicarboxylate, diisopropyl azodicarboxylate, di-tert-butyl azodicarboxylate, and tetramethylazodicarboxamide are preferred, with diisopropyl azodicarboxylate and di-tert-butyl azodicarboxylate are particularly preferred.

The reaction may be performed at 0° C. to 100° C. The reaction temperature is preferably 20° C. to 60° C., particularly preferably 30° C. to 50° C. The reaction time is 1 to 60 hours, preferably 24 to 48 hours.

If required, the reaction may be performed in an inert gas atmosphere such as argon or nitrogen.

In Mitsunobu reaction carried out in this step, cyanomethylenetributylphosphoran or cyanomethylenetrimethylphosphoran may be used instead of the aforementioned phosphorus-containing reagent or azo reagent.

Examples of the solvent employed in this step include toluene, tetrahydrofuran, dioxane, and tert-butyl methyl ether. Of these, toluene and tetrahydrofuran are preferred. The reaction may be performed at 0° C. to 100° C. The reaction temperature is preferably 20° C. to 60° C., particularly preferably 30° C. to 50° C. The reaction time is 1 to 60 hours, preferably 24 to 48 hours.

If required, the reaction may be performed in an inert gas atmosphere such as argon or nitrogen.

3. Step 2

In step 2, the lactone ring of a lactone form (Compound (3)) is opened, to thereby form a halogen form (Compound (4)).

In other words, reaction between Compound (3) and an alcohol $R^4$—OH (wherein $R^4$ has the same meaning as defined above) and a halogenating reagent, to thereby produce Compound (4).

Examples of the halogenating reagent include Lewis acids such as halotrialkylsilane, boron tribromide, and aluminum chloride. Of these, halotrialkylsilane is preferably used.

Examples of the halotrialkylsilane include iodotrimethylsilane, bromotrimethylsilane, and chlorotrimethylsilane. Of these, iodotrimethylsilane and bromotrimethylsilane are preferred, with iodotrimethylsilane being particularly preferred.

Among Lewis acids, boron tribromide is preferably used.

Examples of the alcohol $R^4$—OH (wherein $R^4$ has the same meaning as defined above) include methanol, ethanol, n-propanol, isopropyl alcohol, n-butyl alcohol, isobutyl alcohol, t-butyl alcohol, benzyl alcohol, phenethyl alcohol, phenylpropyl alcohol, and naphthylethyl alcohol. Of these, methanol, ethanol, and phenethyl alcohol are preferred.

The reaction employing the aforementioned halotrialkylsilane as a halogenating agent may be performed by adding a required amount of alcohol to a solution of Compound (3) in solvent, followed by adding a required amount of halotrialkylsilane.

Use of dichloromethane, chloroform, 1,2-dichloroethane, etc. as the reaction solvent is preferred, with dichloromethane and chloroform being particularly preferred.

The reaction may be performed at 0° C. to 50° C. The reaction temperature is preferably 10° C. to 40° C., particularly preferably 20° C. to 30° C. The reaction time is 1 to 24 hours, preferably 3 to 12 hours.

The reaction employing the aforementioned Lewis acid as a halogenating agent may be performed by reacting a required amount of the Lewis acid in a solution of Compound (3) in solvent, followed by reacting a required amount of alcohol.

Examples of the reaction solvent include chloroform, dichloromethane, and carbon tetrachloride. Of these, chloroform and dichloromethane are preferred, with dichloromethane being particularly preferred.

The reaction may be performed at –30° C. to 5° C. The reaction temperature is preferably 0° C. to 30° C. The reaction time is 1 to 24 hours, preferably 6 to 10 hours.

If required, the reactions may be performed in an inert gas atmosphere such as argon or nitrogen.

4. Step 3

In step 3, a halogen form (Compound (4)) is dehalogenated, to thereby produce an ester form (Compound (5)).

In other words, Compound (4) is hydrogenolyzed with a reduction catalyst in the presence or absence of a base, whereby Compound (5) can be produced.

Examples of solvents employed in the reaction include alcohols such as methanol, ethanol, n-propanol, isopropyl alcohol; esters such as methyl acetate, ethyl acetate, and isopropyl acetate; and ethers such as 1,4-dioxane. Of these, methanol, ethanol, n-propanol, isopropyl alcohol, and ethyl acetate are preferred, with methanol and ethanol being particularly preferred.

When the base is present, examples of preferred bases include organic bases such as triethylamine and diisopropylethylamine; and inorganic bases such as sodium hydrogencarbonate and potassium carbonate. Of these, triethylamine, diisopropylethylamine, and potassium carbonate are preferred, with triethylamine being particularly preferred.

Examples of the reduction catalyst include palladium-carbon, platinum oxide, and palladium black, with palladium-carbon being preferred.

The reaction may be performed at 10° C. to 50° C. The reaction temperature is preferably 20° C. to 30° C. The reaction time is 1 to 12 hours, preferably 3 to 6 hours.

5. Step 4

In step 4, an ester form (Compound (5)) is de-esterified, to thereby produce an optically active butyric acid Compound (Compound (6)).

De-esterification may be performed through a conventional method such as hydrolysis or hydrogenolysis (reduction). Hydrolysis may be performed under any of reaction conditions employed for hydrolysis of ester. For example, the hydrolysis is performed in a solvent such as water, an alcohol (e.g., methanol, ethanol, or propanol), an ether (e.g., tetrahydrofuran or dioxane), a ketone (e.g., acetone or methyl ethyl ketone), or acetic acid, or a solvent mixture thereof, in the presence of an inorganic base such as lithium hydroxide, sodium hydroxide, potassium hydroxide, sodium carbonate, or potassium carbonate; a mineral acid such as hydrochloric acid, sulfuric acid, or hydrobromic acid; or an organic acid such as p-toluenesulfonic acid.

Generally, the reaction is performed at 0 to 100° C. for 0.5 to 24 hours, preferably at 10 to 50° C. for 1 to 12 hours.

In an exemplary embodiment of hydrogenolysis, the reaction is performed in an inert solvent such as an ether (e.g., tetrahydrofuran, dioxane, dimethoxyethane, or diethyl ether), an alcohol (e.g., methanol, ethanol, or isopropyl alcohol), or an amide (e.g., dimethylformamide), in the presence of a reduction catalyst such as palladium-carbon, palladium black, palladium, palladium hydroxide, platinum-carbon, platinum oxide, or Raney nickel), in the presence or absence of an inorganic acid such as hydrochloric acid, sulfuric acid, hypochlorous acid or an organic acid such as acetic acid, trifluoroacetic acid, or formic acid, and in a normal pressurized or pressurized hydrogen atmosphere.

Generally, the reaction is performed at 0 to 30° C. for 5 minutes to 24 hours, preferably at 10 to 25° C. for 1 to 12 hours.

Through the aforementioned steps-2 to -4, Compound (6) can be produced at high yield while high optical purity of Compounds (3) to (5) is maintained.

In each reaction step carried out in the present invention, a target substance may be isolated through a routine purification method employed in organic synthesis chemistry such as filtration, washing, drying, re-crystallization, or chromatographic purification, as necessary.

As described in the Examples hereinbelow, according to the process of the present invention, Compound (3) can be produced at high yield and high optical purity, and Compound (6) can be produced while optical purity of Compound (3) is maintained. In the case where Compound (3) is produced from a phenol form and any of the alkylsulfonate derivatives and arylsulfonate derivatives of optically active 2-hydroxybutyrolactone, chemical yield and/or optical purity considerably lowers. Similarly, when the processes disclosed in Patent Document 1 are employed to produce Compound (6); i.e., phenyl-etherification of a phenol form with a 2-halocarboxylic acid ester, phenyl-etherification of a phenol form with a sulfonate derivative of a 2-hydroxycarboxylate, and Mitsunobu reaction between a phenol form and a 2-hydroxycarboxylate are employed, chemical yield and/or optical purity considerably lowers. Therefore, Compound (6) cannot be produced at high chemical yield and high purity through conventional production processes.

Thus, the process of the present invention is remarkably useful for practically producing Compound (6) or a production intermediate therefor.

The present invention will next be described in more detail by way of examples.

EXAMPLES

Production Example 1

Synthesis of (S)-2-trifluoromethanesulfonyloxybutyrolactone

Trifluoromethanesulfonic anhydride (1.65 mL) was gently added to a solution of pyridine (0.83 mL) in dichloromethane mL) at 0° C., and the mixture was stirred for 5 minutes at the same temperature. Subsequently, (S)-2-hydroxybutyrolactone (1.0 g) was added dropwise thereto over 10 minutes at 0° C., followed by stirring for 12 hours at the same temperature. The reaction mixture was filtered through Celite, and the filtrate was concentrated under reduced pressure. The residue was purified through silica gel column chromatography (n-hexane/ethyl acetate=2/1), to thereby yield a colorless oil (1.40 g, 61.2%).

$^1$H-NMR (400 MHz, CDCl$_3$) δ ppm: 2.57-2.67(m, 1H), 2.82-2.90(m, 1H), 4.37(dt, J=10, 6 Hz, 1H), 4.55(dt, J=9, 3 Hz, 1H), 5.46(t, J=9 Hz, 1H).

Example 1

Synthesis of (R)-2-[3-[N-(benzoxazol-2-yl)-N-(3-(4-methoxyphenoxy)propyl)aminomethyl]phenyloxy] butyrolactone (Compound (3))

In an argon atmosphere, N-(benzoxazole-2-yl)-N-(3-(4-methoxyphenoxy)propyl)-3-hydroxybenzylamine (200 mg) was dissolved in dichloromethane (1.5 mL), and triethylamine (0.11 mL) was added dropwise to the solution at room temperature, followed by stirring for 5 minutes at the same temperature. Subsequently, a solution of (S)-2-trifluoromethanesulfonyloxybutyrolactone (174 mg) in dichloromethane (1 mL) was added dropwise to the mixture over 10 minutes at room temperature, followed by stirring for 5 hours at the same temperature. The reaction mixture was added to water (50 mL), and the mixture was extracted with ethyl acetate (30 mL×3). The organic layers were combined and washed with saturated brine, followed by drying over sodium sulfate anhydrate and concentrating under reduced pressure. The residue was purified through silica gel column chromatography (n-hexane/ethyl acetate=1/1), to thereby yield a colorless oil (242 mg, 100', 98.1% ee).

Optical Purity:

Measurement conditions: HPLC

Column: CHIRALPAK AS

Column temperature: 35° C.

Solvent: n-hexane/EtOH=60/40

Flow rate: 1 mL/min

Retention time: 9.37 min (S-form; 6.86 min)

$^1$H-NMR (400 MHz, CDCl$_3$) δ ppm: 2.14(quintet, J=7 Hz, 2H), 2.36-2.44(m, 1H), 2.60-2.67(m, 1H), 3.71(t, J=7 Hz, 2H), 3.76(s, 3H), 3.96(t, J=6 Hz, 2H), 4.25-4.31(m, 1H), 4.43-4.49(m, 1H), 4.77(s, 2H), 4.89(t, J=8 Hz, 1H), 6.81(s, 4H), 6.95-7.03(m, 4H), 7.17(t, J=8 Hz, 1H), 7.22-7.28(m, 2H), 7.37(d, J=8 Hz, 1H).

Example 2

Synthesis of (R)-2-{3-[N-(benzoxazole-2-yl)-N-(3-(4-methoxyphenoxy)propyl)aminomethyl]phenyloxy}butyrolactone (Compound (3))

In an argon atmosphere, N-(benzoxazole-2-yl)-N-(3-(4-methoxyphenoxy)propyl)-3-hydroxybenzylamine (2.0 g), (S)-2-hydroxybutyrolactone (1.0 g), and triphenylphosphine (2.6 g) were dissolved in toluene (30 mL), and a solution of di-tert-butyl azodicarboxylate (2.3 g) in toluene (10 mL) was dropwise to the solution at 0° C., followed by stirring for 24 hours at 40° C. Subsequently, triphenylphosphine (1.3 g) and di-tert-butyl azodicarboxylate (1.1 g) were added to the mixture at 40° C., followed by stirring for 24 hours at the same temperature. The reaction mixture was returned to room temperature. Water was added thereto, and the mixture was extracted with ethyl acetate. The extract was washed with saturated brine. The washed mixture was dried over sodium sulfate anhydrate. The reaction mixture was filtered, and the filtrate was concentrated under reduced pressure. The residue was purified through silica gel column chromatography (n-hexane/ethyl acetate=1/1), to thereby yield a colorless oil (2.2 g, 92%, 98% ee).

Optical Purity:
Measurement conditions: HPLC
　Column: CHIRALPAK AS
　Column temperature: 35° C.
　Solvent: n-hexane/EtOH=60/40
　Flow rate: 1 mL/min
　Retention time: 9.37 min (S-form; 6.86 min)

$^1$H-NMR (400 MHz, CDCl$_3$) δ ppm: 2.14(quintet, J=7 Hz, 2H), 2.36-2.44(m, 1H), 2.60-2.67(m, 1H), 3.71(t, J=7 Hz, 2H), 3.76(s, 3H), 3.96(t, J=6 Hz, 2H), 4.25-4.31(m, 1H), 4.43-4.49(m, 1H), 4.77(s, 2H), 4.89(t, J=8 Hz, 1H), 6.81(s, 4H), 6.95-7.03(m, 4H), 7.17(t, J=8 Hz, 1H), 7.22-7.28(m, 2H), 7.37(d, J=8 Hz, 1H).

Example 3

Synthesis of ethyl (R)-2-{3-[N-(benzoxazol-2-yl)-N-(3-(4-methoxyphenoxy)propyl)aminomethyl]phenyloxy}-4-iodobutylate (Compound (4))

(R)-2-{3-[N-(Benzoxazole-2-yl)-N-(3-(4-methoxyphenoxy)propyl)aminomethyl]phenyloxy}butyrolactone (34.3 g) was dissolved in chloroform (350 mL), and ethanol (21 mL) was added to the solution. Subsequently, in an argon atmosphere, iodotrimethylsilane (26 mL) was gently added to the mixture at 0° C. Thirty minutes after addition, the mixture was stirred for 6 hours at room temperature. The reaction mixture was washed sequentially with 2% aqueous sodium hydrogensulfite solution, water, and saturated brine. The washed reaction mixture was dried over sodium sulfate anhydrate, and concentrated under reduced pressure. The residue was purified through silica gel column chromatography (n-hexane/ethyl acetate=3/1), to thereby yield a colorless oil (41.9 g, 93%).

$^1$H-NMR (400 MHz, CDCl$_3$) δ ppm: 1.78(t, J=7 Hz, 3H), 2.14(quintet, J=7 Hz, 2H), 2.37-2.43(m, 2H), 3.33(t, J=7 Hz, 2H), 3.70(t, J=7 Hz, 2H), 3.76(s, 3H), 3.96(t, J=6 Hz, 2H), 4.09-4.18(m, 2H), 4.70(dd, J=8, 5 Hz, 1H), 4.76(s, 2H), 6.76-6.81(m, 5H), 6.89(s, 1H), 6.93(d, J=8 Hz, 1H), 7.01(t, J=8 Hz, 1H), 7.16(t, J=8 Hz, 1H), 7.22-7.26(m, 2H), 7.37(d, J=8 Hz, 1H).

Example 4

Synthesis of ethyl (R)-2-{3-[N-(benzoxazol-2-yl)-N-(3-(4-methoxyphenoxy)propyl)aminomethyl]phenyloxy}butylate (Compound (5))

Ethyl (R)-2-{3-[N-(benzoxazol-2-yl)-N-(3-(4-methoxyphenoxy)propyl)aminomethyl]phenyloxy}-4-iodobutylate (33.6 g) and triethylamine (22 mL) were dissolved in ethanol (350 mL), and, in an argon atmosphere, a suspension of 10% palladium-carbon (3 g) in ethanol (30 mL) was added to the solution. Subsequently, argon was purged with hydrogen, and the mixture was stirred for 3 hours at room temperature. The reaction mixture was filtered through Celite, and the filtrate was concentrated under reduced pressure. The residue was purified through silica gel column chromatography (n-hexane/ethyl acetate=1/1), to thereby yield a colorless oil (27.8 g, 100%).

$^1$H-NMR (400 MHz, CDCl$_3$) δ ppm: 1.05(t, J=7 Hz, 3H), 1.17(t, J=7 Hz, 3H), 1.96(quintet, J=7 Hz, 2H), 2.14(quintet, J=7 Hz, 2H), 3.70(t, J=7 Hz, 2H), 3.76(s, 3H), 3.96(t, J=6 Hz, 2H), 4.04-4.18(m, 2H), 4.51(t, J=6 Hz, 1H), 4.75(s, 2H), 6.77-6.81(m, 5H), 6.86(s, 1H), 6.90(d, J=8 Hz, 1H), 7.01(dt, J=8 Hz, 1H), 7.16(t, J=8 Hz, 1H), 7.21-7.26(m, 2H), 7.37(d, J=8 Hz, 1H).

Example 5

Synthesis of (R)-2-{3-[N-(benzoxazole-2-yl)-N-(3-(4-methoxyphenoxy)propyl)aminomethyl]phenyloxy}butyric acid (Compound (6))

Ethyl (R)-2-{3-[N-(benzoxazole-2-yl)-N-(3-(4-methoxyphenoxy)propyl)aminomethyl]phenyloxy}butylate (26.0 g) was dissolved in ethanol (200 mL), and 1.5N NaOH (50 mL) was added to the solution, followed by stirring for 1 hour at room temperature. The reaction mixture was washed with diethyl ether, and the formed aqueous layer was acidified with 4N HCl under ice cooling. The thus-treated aqueous layer was extracted with ethyl acetate, and the extract was washed sequentially with water and saturated brine. The washed extract was dried over sodium sulfate anhydrate and concentrated under reduced pressure. The residue was purified through silica gel column chromatography (chloroform/methanol=10/1), to thereby yield the target product (21.3 g, 87%, 98% ee).

Optical Purity:
Measurement conditions: HPLC
　Column: CHIRALPAK AD
　Solvent: n-hexane/IPA/TFA=100/30/0.1
　Flow rate: 2 mL/min
　Retention time: 4.19 min (S-form; 3.68 min)

$^1$H-NMR (400 MHz, CD$_3$OD) δ ppm: 0.94(t, J=7 Hz, 3H), 1.81(m, 2H), 1.99(quintet, J=6 Hz, 2H), 3.60(t, J=7 Hz, 2H), 3.61(s, 3H), 3.85(t, J=6 Hz, 2H), 4.40(t, J=6 Hz, 1H), 4.65(s, 2H), 6.69-6.80(m, 7H), 6.91(dt, J=7, 1 Hz, 1H), 7.05(dt, J=7, 1 Hz, 1H), 7.12-7.18(m, 4H).

Production Example 2

Synthesis of (S)-2-p-toluenesulfonyloxybutyrolactone

Triethylamine (223 mg) was added to a solution of (S)-2-hydroxybutyrolactone (150 mg) in dichloromethane (20 mL) at 0° C. Subsequently, p-toluenesulfony chloride (420 mg) was gently added to the mixture at the same temperature, followed by stirring for 36 hours at room temperature. Water was added to the reaction mixture, and the mixture was extracted with chloroform. The formed chloroform layer was washed with saturated brine. The extract was dried over sodium sulfate anhydrate and concentrated under reduced pressure. The residue was purified through silica gel column chromatography (n-hexane/ethyl acetate=1/1), to thereby yield a white solid (236 mg, 62.7%).

$^1$H-NMR (400 MHz, CDCl$_3$) δ ppm: 2.46(s, 3H), 2.49-2.54(m, 1H), 2.67-2.76(m, 1H), 4.26(td, J=9, 6 Hz, 1H), 4.46(td, J=9, 3 Hz, 1H), 5.07(t, J=8 Hz, 1H), 7.37(d, J=8 Hz, 2H), 7.86(d, J=8 Hz, 2H).

In a manner similar to that employed in Production Example 2, the compounds of Production Examples 3 to 5 were synthesized.

Production Example 3

(S)-2-p-Chlorobenzenesulfonyloxybutyrolactone $^1$H-NMR (400 MHz, CDCl$_3$) δ ppm: 2.44-2.50(m, 1H), 2.71-2.76(m, 1H), 4.29(td, J=9, 7 Hz, 1H), 4.41-4.45(m, 1H), 5.14(t, J=9 Hz, 1H), 7.56(dt, J=9, 2 Hz, 2H), 7.93(dt, J=9, 2 Hz, 2H).

Production Example 4

(S)-2-p-Bromobenzenesulfonyloxybutyrolactone $^1$H-NMR (400 MHz, CDCl$_3$) δ ppm: 2.44-2.50(m, 1H), 2.70-2.75(m, 1H), 4.28(td, J=9, 6 Hz, 1H), 4.42-4.48(m, 1H), 5.17(t, J=9 Hz, 1H), 7.73(dt, J=9, 2 Hz, 2H), 7.84(dt, J=9, 2 Hz, 2H).

Production Example 5

(S)-2-Methanesulfonyloxybutyrolactone $^1$H-NMR (400 MHz, CDCl$_3$) δ ppm: 2.52-2.60(m, 1H), 2.74-2.81(m, 1H), 3.27(s, 3H), 4.34(td, J=10, 6 Hz, 1H), 4.52(td, J=9, 3 Hz, 1H), 5.33(t, J=9 Hz, 1H).

Example 6

Chemical Yield and Optical Purity

Tables 1 and 2 show chemical yield and optical purity of Compound (3x) produced through the process of the present invention (Nos. 1 and 2 in Table 1), of Compound (3x) produced from sulfonate derivatives of optically active 2-hydroxybutyrolactone (Nos. 3 to 8 in Table 1), and of Compounds (5y) and (6y) produced through a process disclosed in Patent Document 1 (Table 2).

As is clear from Tables 1 and 2, the process of the present invention (Nos. 1 and 2 in Table 1) is remarkably excellent in the production of an optically active butyric acid compound and a production intermediate therefor at high yield and high purity.

TABLE 1

| No | A | Reagent | Conditions | Yield (%) | Op. purity (% ee) |
|---|---|---|---|---|---|
| 1 | CF$_3$SO$_3$ | Et$_3$N/CH$_2$Cl$_2$ | rt, 5 hr | 100 | 98 |
| 2 | OH | DBAD, Ph$_3$P/Toluene | 40° C., 2 days | 92 | 98 |
| 3 | CH$_3$SO$_3$ | K$_2$CO$_3$/MeCN | rt, 12 hr | 44 | 11 |
| 4 | 4-CH$_3$PhSO$_3$ | K$_2$CO$_3$/DMF | rt, 2 days | 74 | 62 |
| 5 | 4-CH$_3$PhSO$_3$ | Cs$_2$CO$_3$/MeCN (DMF) | rt, 2 days | 97 | 54 |
| 6 | 4-CH$_3$PhSO$_3$ | K$_2$CO$_3$/MeCN | rt, 12 hr | 51 | 41 |
| 7 | 4-ClPhSO$_3$ | K$_2$CO$_3$/MeCN | rt, 12 hr | 79 | 65 |
| 8 | 4-BrPhSO$_3$ | K$_2$CO$_3$/MeCN | rt, 12 hr | 83 | 68 |

*in 3x denotes the R configuration
DBAD: Di-tert-butyl azodicarboxylate

TABLE 2

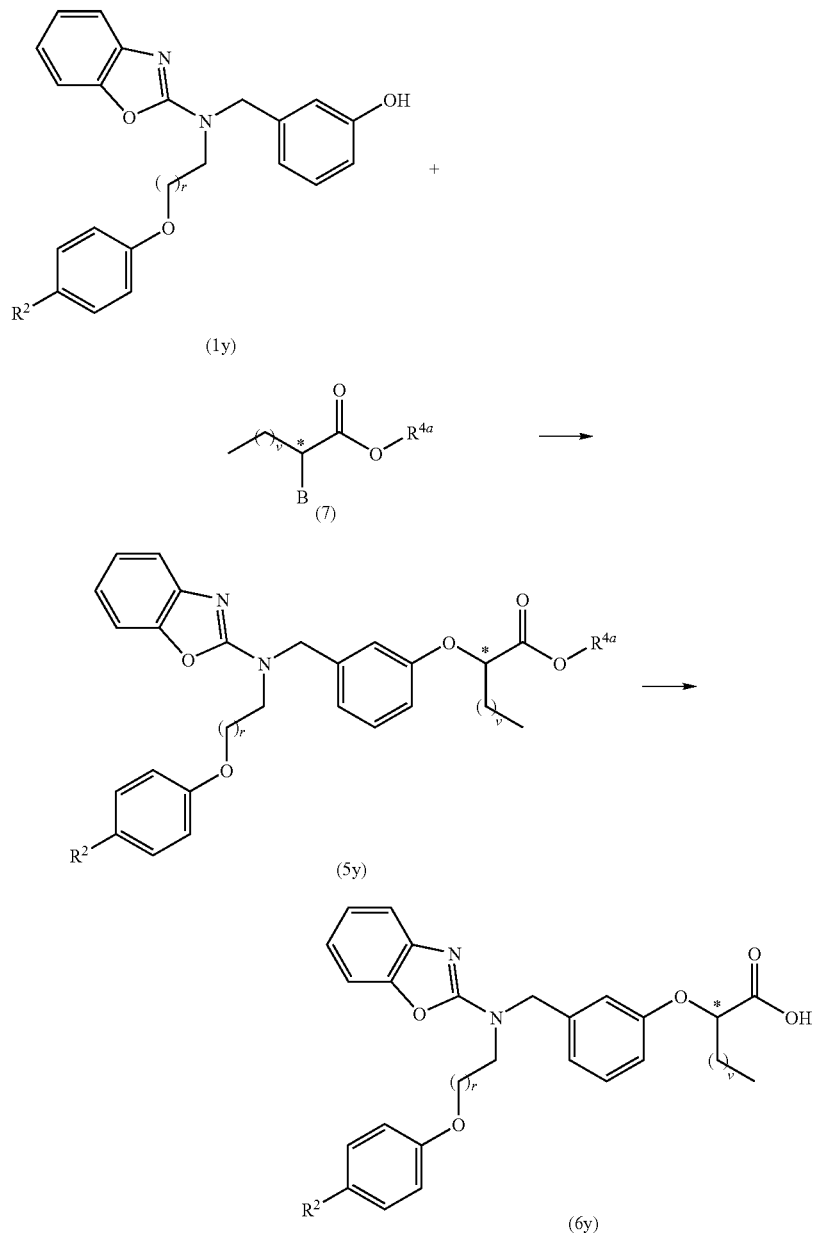

| Compd. (1Y) | | | Compd. (7) | | | | Compd. (5Y) | | Compd. (6Y) Op. purity |
|---|---|---|---|---|---|---|---|---|---|
| No | R² | r | * | R⁴ᵃ | B | v | Reagent | * | Yeild (%) | (% ee) |
| 1 | MeO | 1 | S | Me | Cl | 1 | K₂CO₃ | R | 38 | 13 |
| 2 | MeO | 1 | S | PhCH₂CH₂ | 4-CH₃PhSO₃ | 1 | K₂CO₃ | R | 73 | 92 |
| 3 | Cl | 1 | S | ᵗBu | OH | 1 | DEAD, Ph₃P | R | 44 | 96 |
| 4 | F | 1 | S | ᵗBu | OH | 1 | DEAD, Ph₃P | R | 52 | 96 |
| 5 | MeO | 2 | S | ᵗBu | OH | 1 | DEAD, Ph₃P | R | 60 | 94 |
| 6 | H | 2 | S | ᵗBu | OH | 1 | DEAD, Ph₃P | R | 42 | 95 |
| 7 | F | 2 | S | ᵗBu | OH | 1 | DEAD, Ph₃P | R | 37 | 92 |
| 8 | Cl | 1 | R | ᵗBu | OH | 1 | DEAD, Ph₃P | S | 35 | 96 |
| 9 | F | 1 | R | ᵗBu | OH | 1 | DEAD, Ph₃P | S | 32 | 94 |
| 10 | MeO | 2 | R | ᵗBu | OH | 1 | DEAD, Ph₃P | S | 52 | 91 |
| 11 | H | 2 | R | ᵗBu | OH | 1 | DEAD, Ph₃P | S | 30 | — |
| 12 | MeO | 2 | S | Et | OH | 0 | DEAD, Ph₃P | R | 60 | — |

—: Not measured
DEAD: Diethyl azodicarboxylate

The invention claimed is:

1. A process for producing a compound represented by formula (3):

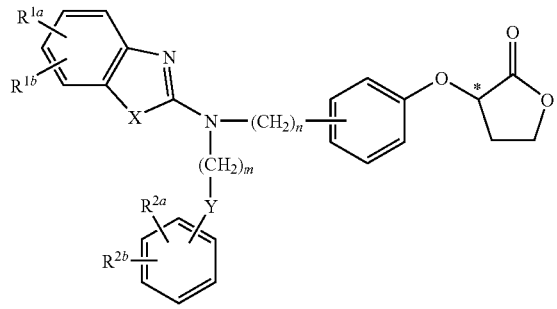

(3)

(wherein $R^{1a}$, $R^{1b}$, $R^{2a}$, and $R^{2b}$, which may be identical to or different from one another, each represents a hydrogen atom, a halogen atom, a nitro group, a $C_{1-4}$ alkyl group, a trifluoromethyl group, a $C_{1-4}$ alkoxy group, a di-$C_{1-4}$ alkylamino group, a $C_{1-4}$ alkylsulfonyloxy group, a $C_{1-4}$ alkylsulfonyl group, or a $C_{1-4}$ alkylthio group, wherein $R^{1a}$ and R1b may be linked to each other to form an alkylenedioxy group, or $R^{2a}$ and $R^{2b}$ may be linked to each other to form an alkylenedioxy group; X represents an oxygen atom, a sulfur atom, or N—$R^3$ (wherein $R^3$ represents a hydrogen atom or a $C_{1-4}$ alkyl group); Y represents an oxygen atom, an S(O)$_l$ group (wherein l is an integer of 0 or 2), a carbonyl group, or a carbonylamino group; n is an integer of 1 to 6; m is an integer of 2 to 6; and the symbol "*" denotes asymmetric S or R configuration), characterized in that the process comprises reacting a compound represented by formula (1):

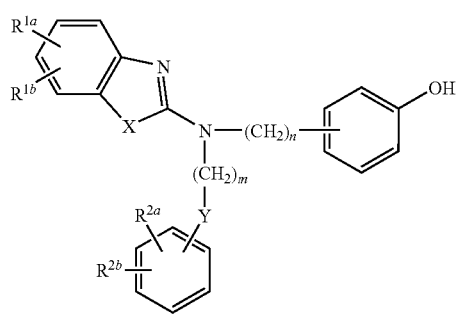

(1)

(wherein $R^{1a}$, $R^{1b}$, $R^{2a}$, $R^{2b}$, X, Y, m, and n have the same meanings as defined above) with optically active 2-trifluoromethanesulfonyloxybutyrolactone represented by formula (2a):

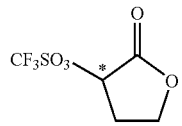

(2a)

(wherein the symbol "*" denotes asymmetric S or R configuration) in the presence of a base, or with optically active 2-hydroxybutyrolactone represented by formula (2b):

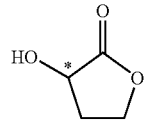

(2b)

(wherein the symbol "*" denotes asymmetric S or R configuration) under Mitsunobu reaction conditions.

2. A process for producing a compound represented by formula (4):

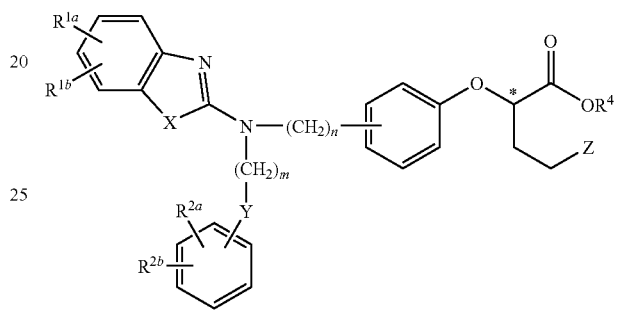

(4)

(wherein $R^{1a}$, $R^{1b}$, $R^{2a}$, and $R^{2b}$, which may be identical to or different from one another, each represents a hydrogen atom, a halogen atom, a nitro group, a $C_{1-4}$ alkyl group, a trifluoromethyl group, a $C_{1-4}$ alkoxy group, a di-$C_{1-4}$ alkylamino group, a $C_{1-4}$ alkylsulfonyloxy group, a $C_{1-4}$ alkylsulfonyl group, or a $C_{1-4}$ alkylthio group, wherein $R^{1a}$ and $R^{1b}$ may be linked to each other to form an alkylenedioxy group, or $R^{2a}$ and $R^{2b}$ may be linked to each other to form an alkylenedioxy group; $R^4$ represents a $C_{1-4}$ alkyl group or a $C_{6-10}$ aryl-$C_{1-3}$ alkyl group; X represents an oxygen atom, a sulfur atom, or N—$R^3$ (wherein $R^3$ represents a hydrogen atom or a $C_{1-4}$ alkyl group); Y represents an oxygen atom, an S(O)$_l$ group (wherein l is an integer of 0 or 2), a carbonyl group, or a carbonylamino group; Z represents a halogen atom; n is an integer of 1 to 6; m is an integer of 2 to 6; and the symbol "*" denotes asymmetric S or R configuration), characterized in that the process comprises reacting a compound represented by formula (1):

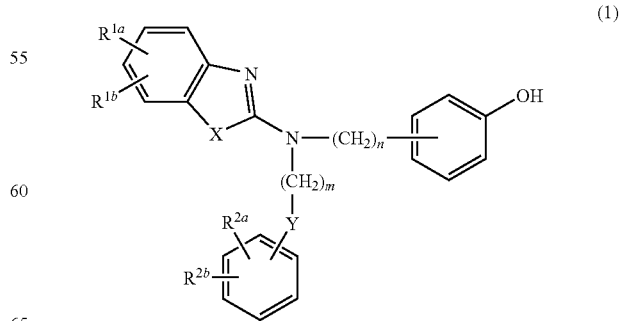

(1)

(wherein $R^{1a}$, $R^{1b}$, $R^{2a}$, $R^{2b}$, X, Y, m, and n have the same meanings as defined above) with optically active 2-trifluoromethanesulfonyloxybutyrolactone represented by formula (2a):

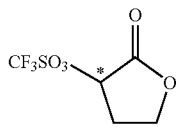

(2a)

(wherein the symbol "*" denotes asymmetric S or R configuration) in the presence of a base, or with optically active 2-hydroxybutyrolactone represented by formula (2b):

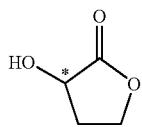

(2b)

(wherein the symbol "*" denotes asymmetric S or R configuration) under Mitsunobu reaction conditions, to thereby form a compound represented by formula (3):

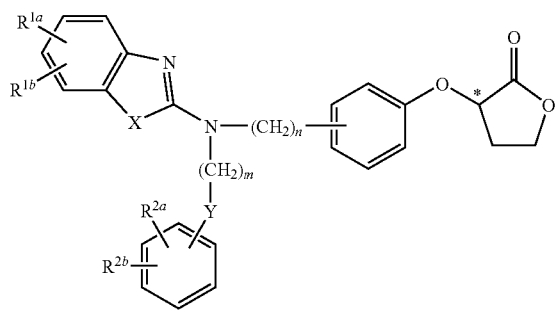

(3)

(wherein $R^{1a}$, $R^{1b}$, $R^{2a}$, $R^{2b}$, X, Y, m, n, and * have the same meanings as defined above), and subsequently, reacting the compound represented by formula (3) with an alcohol represented by $R^4$—OH (wherein $R^4$ has the same meanings as defined above) and a halogenating reagent.

3. A process for producing a compound represented by formula (5):

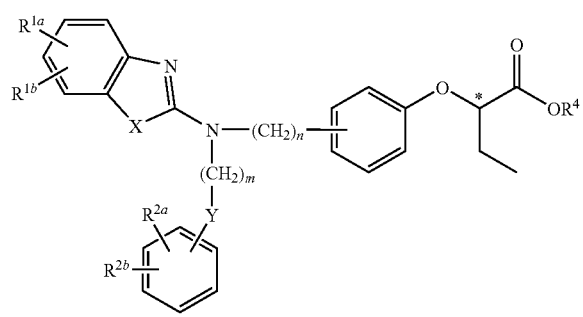

(5)

(wherein $R^{1a}$, $R^{1b}$, $R^{2a}$, and $R^{2b}$, which may be identical to or different from one another, each represents a hydrogen atom, a halogen atom, a nitro group, a $C_{1-4}$ alkyl group, a trifluoromethyl group, a $C_{1-4}$ alkoxy group, a di-$C_{1-4}$ alkylamino group, a $C_{1-4}$ alkylsulfonyloxy group, a $C_{1-4}$ alkylsulfonyl group, or a $C_{1-4}$ alkylthio group, wherein $R^{1a}$ and $R^{1b}$ may be linked to each other to form an alkylenedioxy group, or $R^{2a}$ and $R^{2b}$ may be linked to each other to form an alkylenedioxy group; $R^4$ represents a $C_{1-4}$ alkyl group or a $C_{6-10}$ aryl-$C_{1-3}$ alkyl group; X represents an oxygen atom, a sulfur atom, or N—$R^3$ (wherein $R^3$ represents a hydrogen atom or a $C_{1-4}$ alkyl group); Y represents an oxygen atom, an $S(O)_l$ group (wherein l is an integer of 0 or 2), a carbonyl group, or a carbonylamino group; n is an integer of 1 to 6; m is an integer of 2 to 6; and the symbol "*" denotes asymmetric S or R configuration), characterized in that the process comprises reacting a compound represented by formula (1):

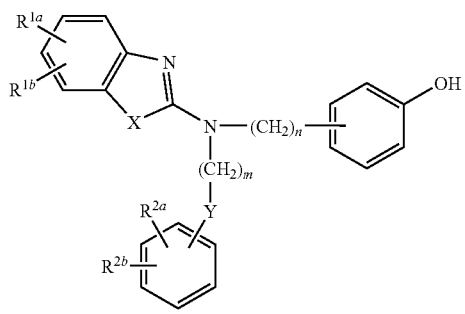

(1)

(wherein $R^{1a}$, $R^{1b}$, $R^{2a}$, $R^{2b}$, X, Y, m, and n have the same meanings as defined above) with optically active 2-trifluoromethanesulfonyloxybutyrolactone represented by formula (2a):

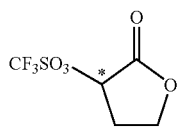

(2a)

(wherein the symbol "*" denotes asymmetric S or R configuration) in the presence of a base, or with optically active 2-hydroxybutyrolactone represented by formula (2b):

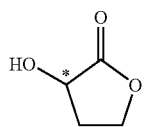

(2b)

(wherein the symbol "*" denotes asymmetric S or R configuration) under Mitsunobu reaction conditions, to thereby form a compound represented by formula (3):

(3)

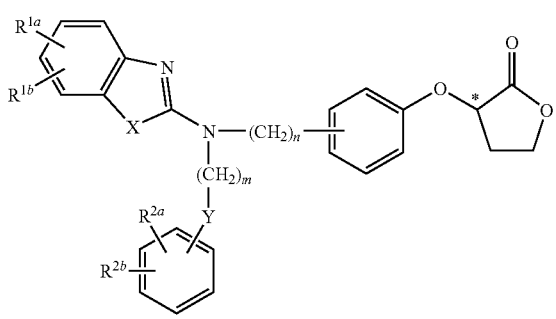

(wherein $R^{1a}$, $R^{1b}$, $R^{2a}$, $R^{2b}$, X, Y, m, n, and * have the same meanings as defined above), subsequently, reacting the compound represented by formula (3) with an alcohol represented by $R^4$—OH (wherein $R^4$ has the same meanings as defined above) and a halogenating reagent, to thereby form a compound represented by formula (4):

(4)

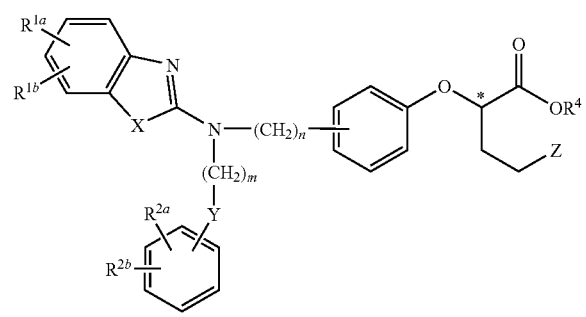

(wherein $R^{1a}$, $R^{1b}$, $R^{2a}$, $R^{2b}$, $R^4$, X, Y, m, n, and * have the same meanings as defined above; and Z represents a halogen atom), and subsequently, dehalogenating the compound represented by formula (4).

4. A process for producing a compound represented by formula (6):

(6)

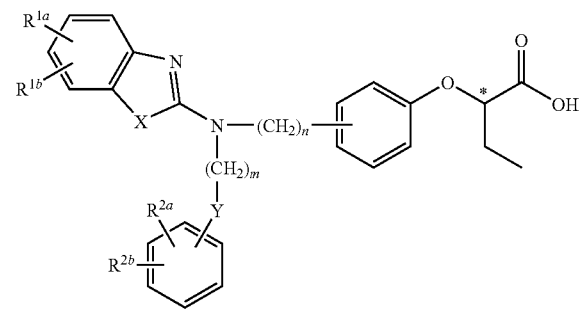

(wherein $R^{1a}$, $R^{1b}$, $R^{2a}$, and $R^{2b}$, which may be identical to or different from one another, each represents a hydrogen atom, a halogen atom, a nitro group, a $C_{1-4}$ alkyl group, a trifluoromethyl group, a $C_{1-4}$ alkoxy group, a di-$C_{1-4}$ alkylamino group, a $C_{1-4}$ alkylsulfonyloxy group, a $C_{1-4}$ alkylsulfonyl group, or a $C_{1-4}$ alkylthio group, wherein $R^{1a}$ and $R^{1b}$ may be linked to each other to form an alkylenedioxy group, or $R^{2a}$ and $R^{2b}$ may be linked to each other to form an alkylenedioxy group; X represents an oxygen atom, a sulfur atom, or N—$R^3$ (wherein $R^3$ represents a hydrogen atom or a $C_{1-4}$ alkyl group); Y represents an oxygen atom, an $S(O)_l$ group (wherein l is an integer of 0 or 2), a carbonyl group, or a carbonylamino group; n is an integer of 1 to 6; m is an integer of 2 to 6; and the symbol "*" denotes asymmetric S or R configuration), characterized in that the process comprises reacting a compound represented by formula (1):

(1)

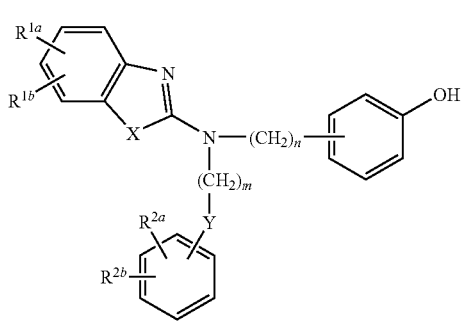

(wherein $R^{1a}$, $R^{1b}$, $R^{2a}$, $R^{2b}$, X, Y, m, and n have the same meanings as defined above) with optically active 2-trifluoromethanesulfonyloxybutyrolactone represented by formula (2a):

(2a)

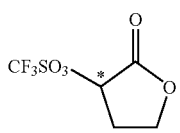

(wherein the symbol "*" denotes asymmetric S or R configuration) in the presence of a base, or with optically active 2-hydroxybutyrolactone represented by formula (2b):

(2b)

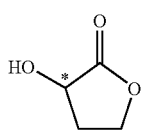

(wherein the symbol "*" denotes asymmetric S or R configuration) under Mitsunobu reaction conditions, to thereby form a compound represented by formula (3):

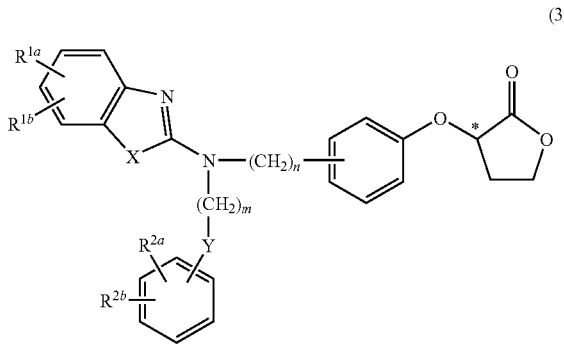

(wherein $R^{1a}$, $R^{1b}$, $R^{2a}$, $R^{2b}$, X, Y, m, n, and * have the same meanings as defined above), subsequently, reacting the compound represented by formula (3) with an alcohol represented by $R^4$—OH (wherein $R^4$ represents a $C_{1-4}$ alkyl group or a $C_{6-10}$ aryl-$C_{1-3}$ alkyl group) and a halogenating reagent, to thereby form a compound represented by formula (4):

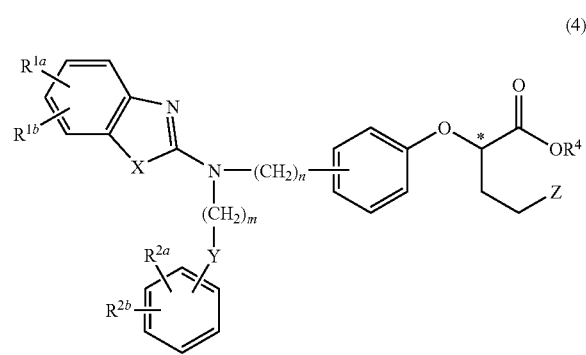

(wherein $R^{1a}$, $R^{1b}$, $R^{2a}$, $R^{2b}$, $R^4$, X, Y, m, n, and * have the same meanings as defined above; and Z represents a halogen atom), subsequently, dehalogenating the compound represented by formula (4), to thereby form a compound represented by formula (5):

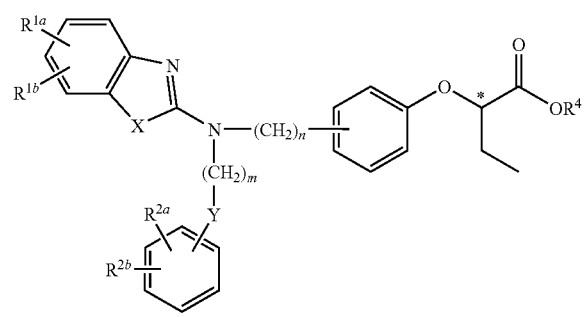

(wherein $R^{1a}$, $R^{1b}$, $R^{2a}$, $R^{2b}$, $R^4$, X, Y, m, n, and * have the same meanings as defined above), and de-esterifying the compound represented by formula (5).

5. A compound represented by formula (3):

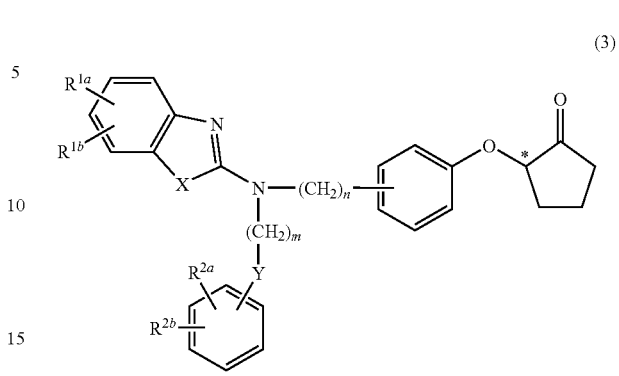

(wherein $R^{1a}$, $R^{1b}$, $R^{2a}$, and $R^{2b}$, which may be identical to or different from one another, each represents a hydrogen atom, a halogen atom, a nitro group, a $C_{1-4}$ alkyl group, a trifluoromethyl group, a $C_{1-4}$ alkoxy group, a di-$C_{1-4}$ alkylamino group, a $C_{1-4}$ alkylsulfonyloxy group, a $C_{1-4}$ alkylsulfonyl group, or a $C_{1-4}$ alkylthio group, wherein $R^{1a}$ and $R^{1b}$ may be linked to each other to form an alkylenedioxy group, or $R^{2a}$ and $R^{2b}$ may be linked to each other to form an alkylenedioxy group; X represents an oxygen atom, a sulfur atom, or N—$R^3$ (wherein $R^3$ represents a hydrogen atom or a $C_{1-4}$ alkyl group); Y represents an oxygen atom, an $S(O)_l$ group (wherein l is an integer of 0 or 2), a carbonyl group, or a carbonylamino group; n is an integer of 1 to 6; m is an integer of 2 to 6; and the symbol "*" denotes asymmetric S or R configuration).

6. A compound represented by formula (4):

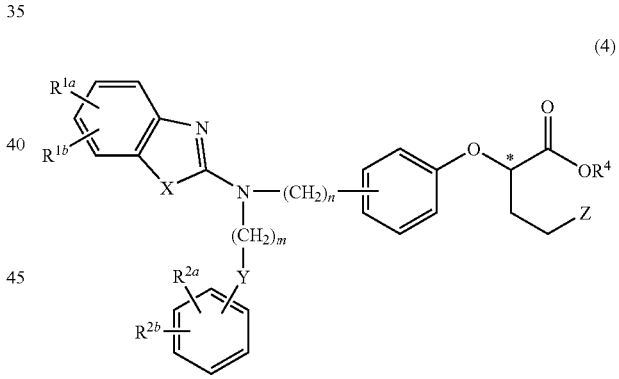

(wherein $R^{1a}$, $R^{1b}$, $R^{2a}$, and $R^{2b}$, which may be identical to or different from one another, each represents a hydrogen atom, a halogen atom, a nitro group, a $C_{1-4}$ alkyl group, a trifluoromethyl group, a $C_{1-4}$ alkoxy group, a di-$C_{1-4}$ alkylamino group, a $C_{1-4}$ alkylsulfonyloxy group, a $C_{1-4}$ alkylsulfonyl group, or a $C_{1-4}$ alkylthio group, wherein $R^{1a}$ and $R^{1b}$ may be linked to each other to form an alkylenedioxy group, or $R^{2a}$ and $R^{2b}$ may be linked to each other to form an alkylenedioxy group; $R^4$ represents a $C_{1-4}$ alkyl group or a $C_{6-10}$ aryl-$C_{1-3}$ alkyl group; X represents an oxygen atom, a sulfur atom, or N—$R^3$ (wherein $R^3$ represents a hydrogen atom or a $C_{1-4}$ alkyl group); Y represents an oxygen atom, an $S(O)_l$ group (wherein l is an integer of 0 or 2), a carbonyl group, or a carbonylamino group; Z represents a halogen atom; n is an integer of 1 to 6; m is an integer of 2 to 6; and the symbol "*" denotes asymmetric S or R configuration).

* * * * *